United States Patent [19]
Ruetschi et al.

[11] Patent Number: 6,090,053
[45] Date of Patent: Jul. 18, 2000

[54] DENTAL DEVICE AND METHOD AND ALSO REFERENCE ELECTRODE FOR DETERMINING THE STATE OF A TOOTH CROWN OR TOOTH BRIDGE

[75] Inventors: Paul Ruetschi, Grandevent; Charles Ruetschi, Murten, both of Switzerland

[73] Assignee: Ruetschi Praezisions-Technologie AG, Muntelier, Switzerland

[21] Appl. No.: 09/204,240

[22] Filed: Dec. 3, 1998

[30] Foreign Application Priority Data

Dec. 5, 1997 [CH] Switzerland ............................ 2822/97

[51] Int. Cl.$^7$ .................................................. A61B 5/103
[52] U.S. Cl. ........................................... 600/590; 433/215
[58] Field of Search .............................. 600/590; 432/215

[56] References Cited

U.S. PATENT DOCUMENTS 5,380,422  1/1995  Negishi et al. .

FOREIGN PATENT DOCUMENTS 0 283 962  9/1988  European Pat. Off. .
0 446 874  9/1991  European Pat. Off. .

OTHER PUBLICATIONS

K. Arvidson, Swed. Dent. J., vol. 68, pp. 41–46, "In Vitro Corrosion Studies of a Dental Gold Alloy in Contact with Cohesive Gold and Amalgam", 1975.

K. Arvidson, Swed. Dent. J., vol. 68, pp. 135–139, "Corrosion Studies of a Dental Gold Alloy in Contact with Amalgam Under Different Conditions", 1975.

M. Bergman, et al., Scand. J. Dent. Res., vol. 86, pp. 135–145, "Potential and Polarization Measurements In Vivo of Oral Galvanism", 1978.

G.J. Ewers, et al., Journal of Oral Rehabilitation, vol. 12, pp. 469–476, "The Electrochemical Activity of the Oral Cavity—A New Approach", 1985.

K. Nilner, et al., Scand. J. Dent. Res., vol. 93, pp. 357–359, "Electrochemical Potentials of Amalgam Restorations in Vivo", 1985.

E. Yontchev, et al., Journal of Oral Rehabilitation, vol. 13, pp. 365–382, An Examination of the Surface Corrosion State of Dental Fillings and Constructions, 1986.

A.W.J Muller, et al., Journal of Oral Rehabilitation, vol. 16, pp. 271–277, "The Determination of the Electrical Potential of a Metallic Restoration in the Oral Cavity", 1989.

Shigemitsu Nomoto, et al. "Micro–Probe for Measurement of Corrosion Potential of Metallic Restorations in Mouth", Materials Science, vol. 58 No. 7, Jul. 1979, pp. 1688–1690.

Roy Holland, "Galvanic Currents Between Gold and Amalgam", Scand. J.. Dent. Res., vol. 88, 1980, pp. 269–272.

Maud Bergman, "American Dental Association Status Report on the Occurrence of Galvanic Corrosion in the Mouth and its Potential Effects", JADA, vol. 115, Nov. 1987, pp. 783–786.

*Primary Examiner*—Cary O'Connor
*Assistant Examiner*—Pamela Wingood
*Attorney, Agent, or Firm*—Oblon, Spivak, McClelland, Maier & Neustadt, P.C.

[57] ABSTRACT

The dental device for determining the state of an at least partially metal tooth crown (2) or tooth bridge (2) of a tooth (1) comprises a scanning electrode (3) with which an electrical contact to the tooth crown (2) or tooth bridge (2) can be established, an active part (10) of a reference electrode (9), which active part (10) can be placed in the mouth, and a voltage meter (12) which can be connected electrically to the scanning electrode (3) and the reference electrode (9) and allows their potential difference to be measured, the voltage meter (12) having an input resistance of in particular more than $10^6 \Omega$. The active part (10) of the reference electrode (9) consists in particular of a silver wire coated with silver chloride. The holder (13) of the reference electrode (9) can be plastically deformed as desired and can be fitted in the mouth of a patient.

30 Claims, 4 Drawing Sheets

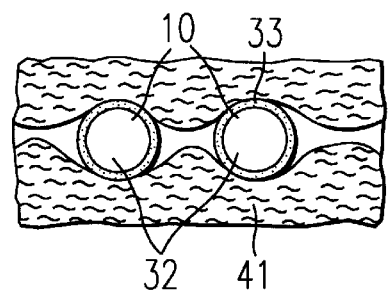
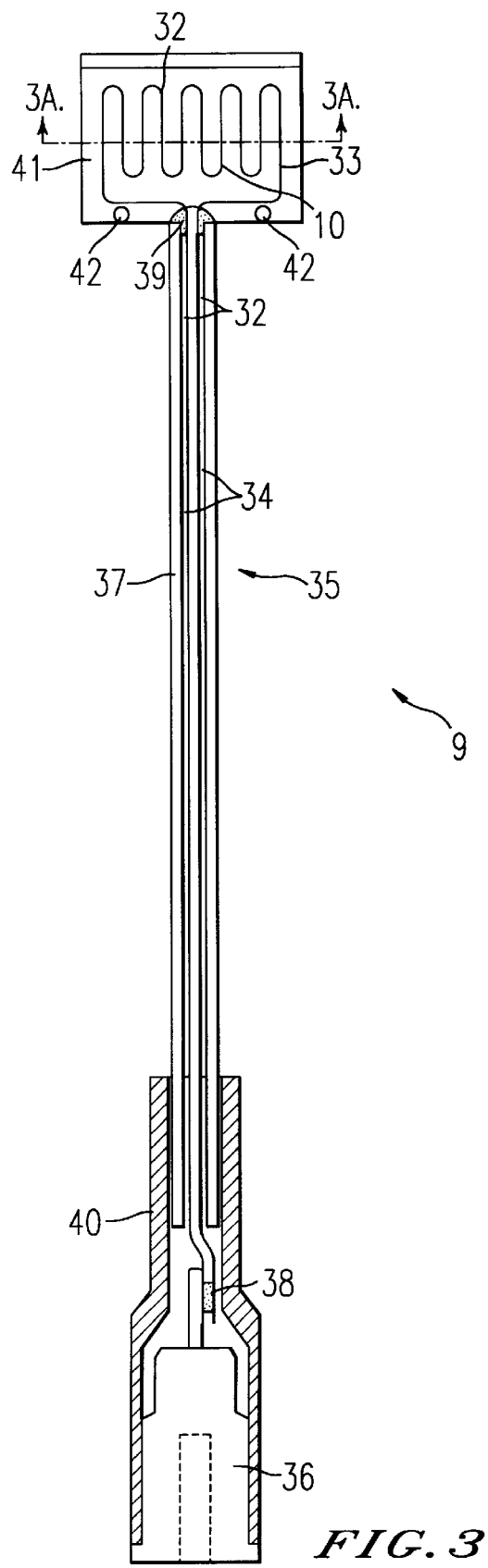
FIG. 3A
FIG. 3

DENTAL DEVICE AND METHOD AND ALSO REFERENCE ELECTRODE FOR DETERMINING THE STATE OF A TOOTH CROWN OR TOOTH BRIDGE

BACKGROUND OF THE INVENTION

1. Field of the Invention

The invention relates to a dental device and a method for determining the state of an at least partially metal tooth crown or tooth bridge. The invention further relates to a dental reference electrode for the dental device and the method.

2. Discussion of the Background

For a long time, tooth crowns or tooth bridges consisting at least partially of metal were fitted on teeth without the complete removal of any amalgam fillings which may have been present. If amalgam comes into direct contact with, for example, gold crowns or gold bridges, accelerated anodic corrosion of the amalgam can take place. The products of corrosion of the amalgam, for example copper ions, tin ions, silver ions or mercury ions, can have a toxic action on the gum. In some circumstances, so much mercury is released that dangerous mercury allergies and serious disturbances of the central nervous system occur. Mercury ions pass through the bloodstream and the blood/brain barrier into the brain, the critical organ for accumulation of mercury. For this reason, it is advisable to completely remove amalgam which is located underneath an at least partially metal tooth crown, such as a gold crown.

Unfortunately, however, it has not hitherto been possible to detect the presence of amalgam without destroying and dismantling the tooth crown or tooth bridge. Conclusive X-ray pictures cannot be taken because a gold crown provides too much shielding against the X-rays, with the result that no contrast can be obtained for the amalgam which may be present.

SUMMARY OF THE INVENTION

The object of the present invention is to propose a device and a method for determining the state of a tooth crown or tooth bridge, by which method it is possible to detect the presence of amalgam.

A further object of the present invention is to create a robust, precise, practical and inexpensive dental reference electrode, in particular for the device and for the method for determining the state of a tooth crown or tooth bridge.

This object is achieved with a device having the features of claim 1. Subclaims 2 through 8 relate to further advantageous embodiments of the device. The object is further achieved using a method having the features of claim 9. Subclaims 10 through 13 relate to further advantageous embodiments of the method. The object is further achieved with a dental reference electrode having the features of claim 14. Subclaims 15 through 21 relate to further advantageous embodiments of the reference electrode.

A tooth crown or tooth bridge is more generally referred to as a restoration, the restoration usually consisting of metal or consisting at least partially of metal, and in particular a noble metal such as, for example, gold. In addition, for example for esthetic reasons, a metal restoration of this kind can be provided with a nonmetal coating such as ceramic or porcelain, so that the overall restoration consists at least partially of metal, but additionally comprises further nonmetal components. As a restoration for teeth, a crown or bridge made of a gold alloy is the longest lasting and most attractive solution, but also the most expensive one. The visible parts of the tooth are in most cases covered with a coating of, for example, ceramic or porcelain, which is esthetically pleasing.

For a long time, restorations consisting at least partially of metal, in particular restorations of noble metal, such as tooth crowns or tooth bridges, were mounted on teeth without complete removal of any amalgam fillings which may have been present. In doing so, too little account was taken of the danger of the formation of so-called local elements. It is true that a tooth cement, used to secure a tooth crown or tooth bridge, forms an insulating layer between the tooth crown or tooth bridge and the amalgam filling. However, an insulating effect is often not guaranteed in the longer term, for example if the layer of cement is partially destroyed by years of erosion. As a result of the direct contact between the metal tooth crown or tooth bridge, consisting in particular of gold or a noble metal alloy, and the amalgam, a local element is formed which causes accelerated corrosion of the amalgam and possibly of the tooth crown.

The invention is based on the recognition that the electrode potential of the tooth crown can be measured using a measurement device, and that from the measured potential or measured voltage it is possible to obtain an indication as to the presence of an anodic reaction underneath the tooth crown or tooth bridge.

One advantage of the invention is that if an anodic reaction is detected, it is possible to conclude that amalgam is present. A further advantage of the invention is that conclusions can be drawn concerning the extent of the corrosion based on the measured value of the electrode potential. An important advantage of the invention is that it is possible to detect amalgam under an at least partially metal restoration, such as a tooth crown or a tooth bridge, and the extent of the corrosion without removing the tooth crown or tooth bridge. The invention permits rapid and nondestructive testing of the state of a tooth crown or tooth bridge and of any amalgam present, or generally of the state of the tooth, and thus provides an indication as to the necessity of dismantling the tooth crown or tooth bridge for the purpose of restoration or extraction of the underlying tooth in question. This advantage is of crucial economic importance because in the past, in order to determine the state of an at least partially metal restoration such as a crown, it was necessary to remove the latter from the tooth. Especially if it was found, after such an intervention, that the crown was in a perfectly satisfactory state, unnecessary costs had been incurred and, above all, the patient had been caused unnecessary inconvenience. A further advantage of the invention is that a dentist is able to decide very quickly, and in a painless way for the patient, whether a new restoration or even an extraction of a tooth is necessary. This permits quicker and less expensive treatment. In addition, if it is decided that an extraction is necessary, it is possible to dispense with preliminary dismantling of the tooth crown.

The anodic reaction can also indicate corrosion of the tooth crown or tooth bridge itself or indicate oxidizing organic constituents.

The object of the invention is also in particular achieved by means of a dental reference electrode for electrochemical potential measurement in the oral cavity, said reference electrode comprising an electrochemically active part consisting of a silver wire coated with silver chloride, the silver wire being designed in particular in the form of a single or multiple loop.

In a particularly advantageous embodiment, the dental reference electrode comprises an absorbent sheath which is made, in particular, of electrically insulating fibers and covers the active part, and also a plastically or elastically deformable shaft in the inside of which an electrical connection, connecting the active part to a plug socket, is arranged to run electrically insulated from the outside.

Advantages of the dental reference electrode according to the invention are that it is robust and accurate, it is practical to use, it can be produced inexpensively, and it can be designed for one-off use as a disposable reference electrode for dental applications. With the reference electrode according to the invention, electrochemical or galvanic potentials of at least partially metal restorations in the oral cavity can be determined quickly, accurately, with minimal effort and inexpensively. The measured potentials can give a physician additional information on the state of at least partially metal restorations. In particular, the measured potentials give indications of corrosion processes which are going on hidden underneath crowns or bridges. It is known that as a result of such corrosion processes, ions of the elements mercury, cadmium, copper, silver and zinc etc. can be released in the oral cavity, and this can trigger allergic or toxic reactions. Such corrosion products can also pass via the saliva into the digestive tract, and from there to other parts of the human body, where they can undesirably accumulate.

BRIEF DESCRIPTION OF THE DRAWINGS

In the illustrative embodiments which follow, the nature of the metal tooth crown or tooth bridge is explained on the basis of a gold crown. Therefore, where mention is made of a gold crown, this also always includes a noble metal alloy used in dentistry. In the drawing:

FIG. 3 shows a view of a reference electrode;

FIG. 3a shows a partial view of a section through the reference electrode along the line A—A in FIG. 3;

Tab. 1 gives an overview of the measurement results obtained.

DESCRIPTION OF THE PREFERRED EMBODIMENTS

Figure 1:
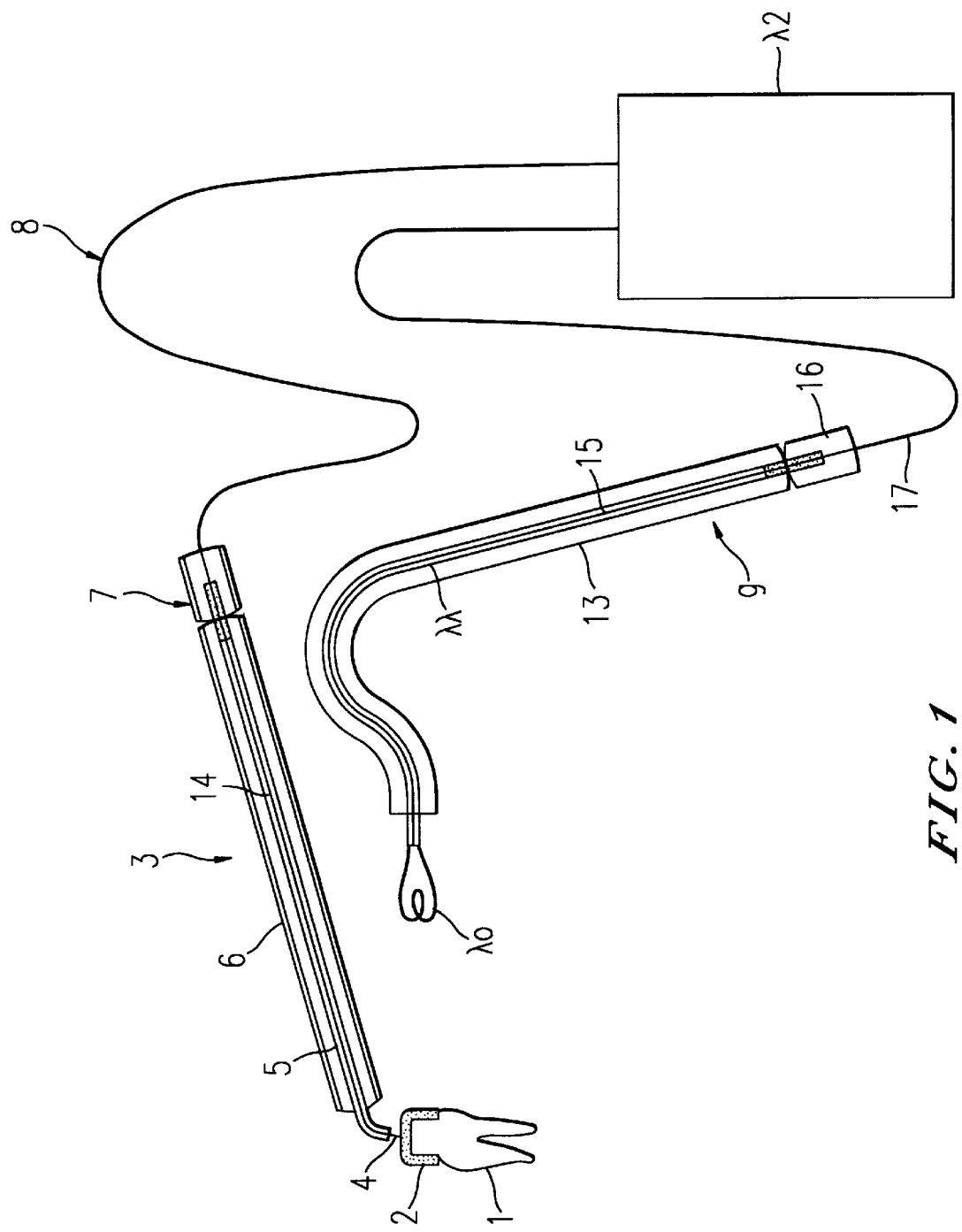
FIG. 1 shows a diagrammatic view of a device according to the invention.

FIG. 1 shows the device according to the invention. The tooth 1 to be tested, with gold crown 2 or tooth bridge 2, is contacted via a tip-shaped contact 4 of a scanning electrode 3. The tip consists of a gold alloy which can be similar to the crown material. The tip can also be provided with a layer of gold or a gold alloy only on its surface. The diameter of the tip is smaller than 2 mm, at the frontmost end preferably smaller than 0.5 mm. With the scanning electrode 3, an electrical connection is established with the gold crown 2 or tooth bridge 2 via the contact 4, in which case the gold crown 2 or tooth bridge 2 constitutes the actual electrode, i.e. the transition from metallic conductor to conduction by ions.

The contact tip 4 can also be a small cylindrical pin which is insulated with plastic on the cylindrical outside. The contact pin 4 is connected to an electrical lead 14 which is arranged to run through the inside of the scanning electrode 3. This lead 14, designed as a metal wire, is surrounded by insulation 5. Thus, with the exception of the contact tip 4, the scanning electrode 3 has a high level of electrical insulation from the outside. The contact tip 4 protrudes less than 5 mm from the insulation 5. A grip 6 surrounds the insulation 5 and is also ergonomically designed in such a way that the scanning electrode 3 lies easily and comfortably in the hand. The insulation 5 can form part of the grip 6. The electrical lead 14 is connected to a plug socket 7. The plug socket 7 is connected to a voltage meter 12 via a connection cable 8 which is electrically insulated from the outside.

The device moreover comprises a reference electrode 9. In the illustrative embodiment shown, the reference electrode 9 has at its front end an active part 10 consisting of a silver wire 10 which is coated with silver chloride and is appropriately shaped in such a way that the active part 10 can be placed in the mouth of a patient. The silver wire 10 is connected to an electrically conducting lead 15, which lead 15, designed as a metal wire, runs with a high level of electrical insulation through the inside of the reference electrode 9. The insulation 11 surrounds the lead 15. The insulation 11 can be integrated in the holder 13 of the reference electrode 9. Except for the active part 10, the reference electrode 9 has a high level of electrical insulation from the outside. The reference electrode 9 can be designed in such a way that it is suitable for fitting in a lower jaw, the active part 10 coming to lie in the mouth, preferably under the tongue. The silver wire 10 coated with silver chloride is placed in the mouth in such a way that it does not touch any tooth crown or tooth bridge, for example under the tongue. To avoid contact with other gold crowns or gold bridges and to ensure moistening, the silver wire 10 can be covered with a coating of absorbent gauze, pad or tissue. The gauze, the pad or the tissue is saturated, for example, with a dilute NaCl solution before the active part 10 is placed in the mouth. Such moistening has the further advantage that the active part 10 is arranged in the mouth in a defined electrolyte solution, this affording a stable potential, so that the pH value in the mouth or the chloride concentration of the saliva has only a small effect on the potential of the reference electrode 9 or active part 10.

A wire or electrode of silver/silver chloride has proven useful for the active part 10 of the reference electrode 9. Instead of a silver/silver chloride electrode, other reference electrodes 9 could also in principle be used. Suitable reference electrodes 9 are generally those with an active part 10 of metal/metal chloride.

The lead 15 of the reference electrode 9 is provided with a plug socket 16 at the rear end. The plug socket 16 is releasably connected to the voltage meter 12 via a connection cable 17 which is electrically insulated from the outside.

The voltage meter 12 is able to determine the potential difference, or the voltage, between the scanning electrode 3 and the reference electrode 9, or between the contact tip 4 and the active part 10, the voltmeter 12 being designed, for example, as a millivolt meter with an input resistance of more than $10^6$ ohm. The voltmeter 12 has a display (not shown) for showing the measured voltage or for showing the state of the tooth crown or tooth bridge. The voltage meter can also have electronic components such as voltage dividers or amplifier circuits, and in particular also digital electronics, or a micro-processor.

For esthetic reasons, tooth crowns 2 or tooth bridges 2 are often covered completely, or only on the outer aspect, with a porcelain or ceramic layer, for example. The device according to the invention can also be used in these cases. To do so, a small hole is bored through the porcelain or ceramic layer as far as the gold support, through which hole the contact tip 4 of the scanning electrode 3 is passed, and the layer of gold can be contacted. The hole is not of importance as regards the life of the tooth. After the measurement, the hole can be cemented back up again.

When measuring the electrode potential, saliva plays the role of electrolyte. In this context it should be noted that the potential of the gold crown 2 or gold bridge 2, as measured by means of the scanning electrode 3, depends on the pH, while that of the reference electrode 9 or active part 10 depends on the concentration of chloride ions. To reduce the influence of these factors, the oral cavity can be rinsed in advance with a suitable solution. Such a solution would be, for example, a dilute sodium chloride solution buffered with lactic acid.

The illustrative embodiment of a reference electrode 9, shown in FIG. 3, has, at the front end, an active part 10 with a silver wire 32 which has been bent to form a loop. In the area of this active part 10 with loops, the silver wire 32 is covered with a layer of silver chloride 33. An electrical connection 34 runs through the inside of the shaft 35 between the active part 10 and a plug socket 36. In the illustrative embodiment according to FIG. 3, the electrical connection 34 consists of a doubled back silver wire 32. The latter is connected to the plug socket 36 via a solder point 38. Along the entire length of the shaft 35, the silver wire 32 running inside it is surrounded by a high-insulation silicone tubing 37. At the front end of the shaft 35, the silver wire 32 is sealed into the silicone tubing 37 with a silicone adhesive 39. A cylindrical plastic part 40 surrounds and insulates from the outside the solder point 38, a part of the plug socket 36 and the rear part of the silicone tubing 37. The plastic part consists, for example, of polyacetal copolymer. The thickness of the electrical connection 34 is preferably chosen such that it gives the shaft 35 additional stability and also a plastic or elastic deformability, with the result that the shaft 35 can be bent as desired and fitted in the mouth of a patient, in the same way as a saliva ejector. For this purpose, the doubled back silver wire 32 in the shaft 35 has a diameter of between 0.6 and 1.2 mm. In the area of the active part 10 comprising a single or multiple loop of silver wire 32, the silver wire 32 is covered with a silver chloride layer 33, as is shown in FIG. 3a in a section through two silver wires 32 on an enlarged scale, and this silver chloride layer 33 has a thickness of preferably between 1 $\mu$m and 5 $\mu$m. The silver chloride layer 33 can be produced, for example, by anodizing in dilute chloride solution. The loop-shaped part 10 coated with silver chloride represents the electrochemically active surface of the reference electrode 9. This part 10 is covered with an absorbent sheath 41 of insulating fibers. This sheath 41 preferably consists of an absorbent felt or fleece of cotton fibers. The absorbent fleece 41 preferably has a thickness of more than 0.5 mm and can absorb at least 0.1 g of water per $cm^2$. Along the edge, the absorbent fleece 41 is bonded or sewn at individual points 42 so that it cannot be scraped off the loop-shaped active part 10. The absorbent fleece 41 surrounds the loop of silver wire in such a way that a direct electrical contact between the loop and an at least partially metal restoration in the oral cavity is rendered impossible.

The reference electrode 9 according to the invention has significant advantages in being very robust. The reference electrode 9 according to the invention does not comprise any parts made of glass, is shockproof and breakproof, and is also light and manageable. The reference electrode 9 has very good stability and current-carrying capacity, in particular also as a result of the loop-shaped design of the electrochemically active part 10. The electrochemically active part 10 does not have a pointed end, as a result of which stab injuries are rendered impossible. As a result of the loop-shaped design, the silver chloride layer 33 has a uniform thickness, by which means peeling-off is avoided.

A further advantage of the reference electrode 9 according to the invention is its ease of handling, which, by virtue of the bendable shaft, allows it to be placed under the tongue in the same way as a saliva ejector. A physician does not therefore have to hold the reference electrode 9 in his hand during the measurement. A further practical advantage is that the reference electrodes 9 can be stored in the dry state for months prior to use. They are preferably kept in sealed plastic film packages. Directly before use, the reference electrode 9 is removed from the package and connected to the voltage meter 12 via the connection cable 17. The active part 10 which is covered with the absorbent sheath 41 is then dipped for a few seconds into a dilute, calibrated standard solution with chloride ions. The chloride ion solution should have a concentration at least corresponding to, or in excess of, that of natural saliva. In practical tests, a concentration of 0.05 mol/liter has proven suitable. While it is being immersed, the absorbent sheath 41 becomes saturated with electrolyte solution. In this way a uniform wetting of the silver chloride layer 33 is ensured. The absorbent sheath 41, for example a fleece of cotton fibers, absorbs so much electrolyte that the concentration during the short time (a few seconds) of the measurement remains constant on the active surface and is exactly defined. The sheath 41 saturated with electrolyte also guarantees an extensive electrolytic contact surface for the saliva of the oral cavity. Since the absorbent sheath is electrically nonconductive, a direct electrical contact between the loop of silver wire of the active part 10 and an at least partially metal restoration is rendered impossible. The reference electrode 9 according to the invention permits an extraordinarily low-resistance measuring circuit.

A further advantage of the design according to FIG. 3 is the large distance between the electrolyte-saturated sheath 41 and the solder point 38 to the plug socket 36. This affords additional safety ensuring that no electrolyte or saliva can reach the solder point 38 during use. If the electrolyte were to reach the solder point, this could cause electrochemical reactions there which could adulterate the potential measurements.

Figure 4:
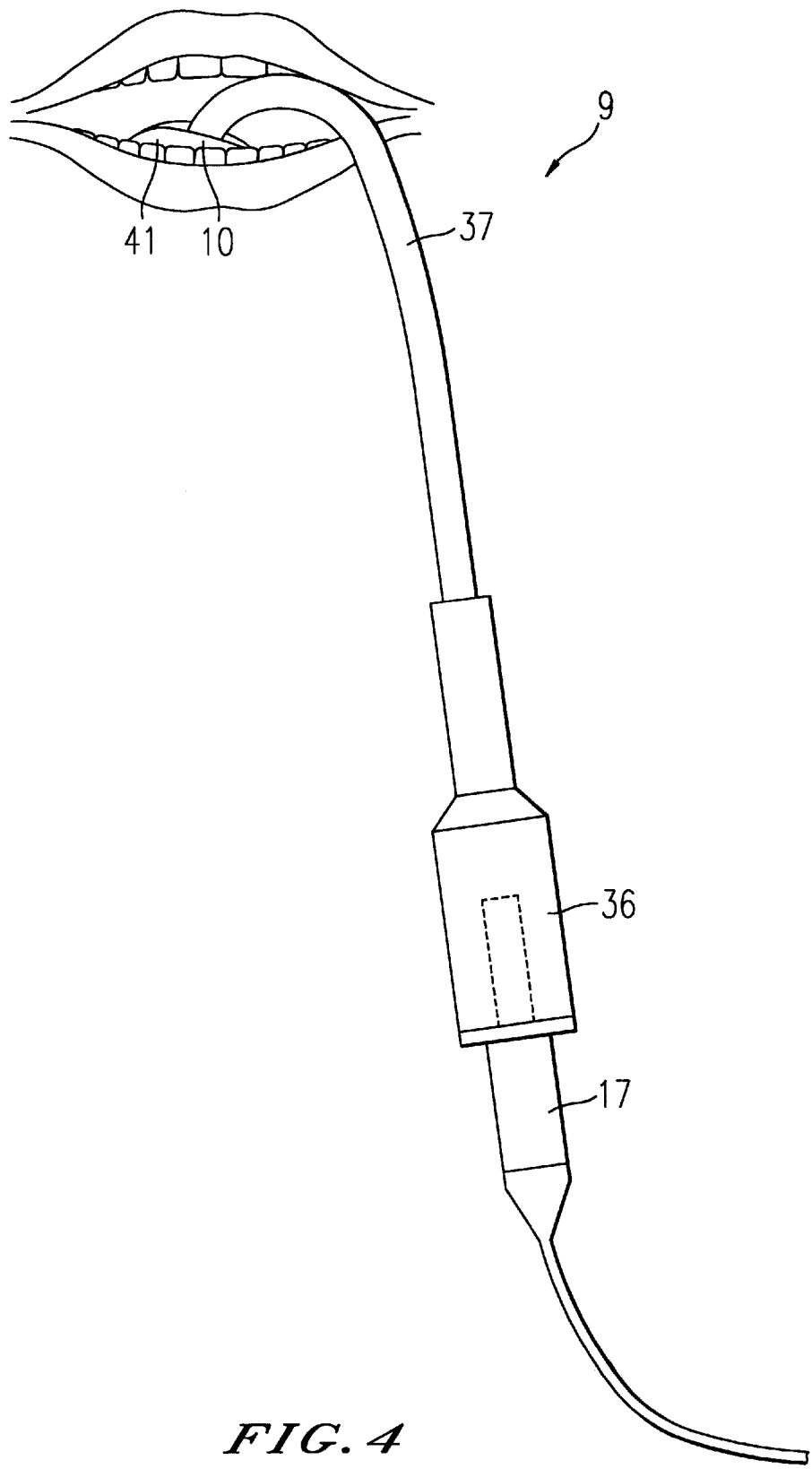
FIG. 4 shows a reference electrode placed in a mouth.

A further advantage of the reference electrode 9 according to the invention is that it can be manufactured in series production at a very favorable cost. It is therefore suitable for one-off use. It can be packaged and stored in the dry state and, when needed, is very quickly ready to use. It suffices to dip the electrochemically active part 10 with sheath 41 in electrolyte solution for a few moments, this electrolyte solution being supplied together with the reference electrode 9. To measure the potential of at least partially metal restorations, the active part 10 with sheath 41 is placed in the mouth, preferably under the tongue, and the shaft 35 is bent in the desired manner, as is represented in FIG. 4. Using a scanning electrode 3 with noble metal tip 4, with which the at least partially metal restoration to be tested is contacted, the electrochemical potential of the restoration can be measured. The measurement requires only a few seconds.

Table I shows experimental results which were measured using the device according to FIG. 1. For the measurements carried out on tooth bridges provided with a porcelain covering, a small hole was bored through the latter as far as the gold support. The measured potentials were in the range of between 0 and −0.250 volts (using a silver/silver chloride reference electrode in 0.05 molar chloride solution). After measurement of the potential, the tooth bridge 2 or tooth crown 2 in question was dismantled and the state of the underlying tooth 1 was analyzed. Residues of amalgam and the inner side of the crown or bridge were examined by X-ray fluorescence spectroscopy. There is a clear correlation between the measured potential and the state of the tooth crown 2 or tooth bridge 2, or of the amalgam filling 21 covered at least partially by a tooth crown 2 or tooth bridge 2. At potentials which were lower than −0.150 volts, the presence of amalgam and signs of corrosion were observed. By contrast, the state of the tooth or of the tooth crown or tooth bridge was satisfactory or perfect and no corroding amalgam was observed at potentials between 0 and −0.150 volts.

Figure 2:
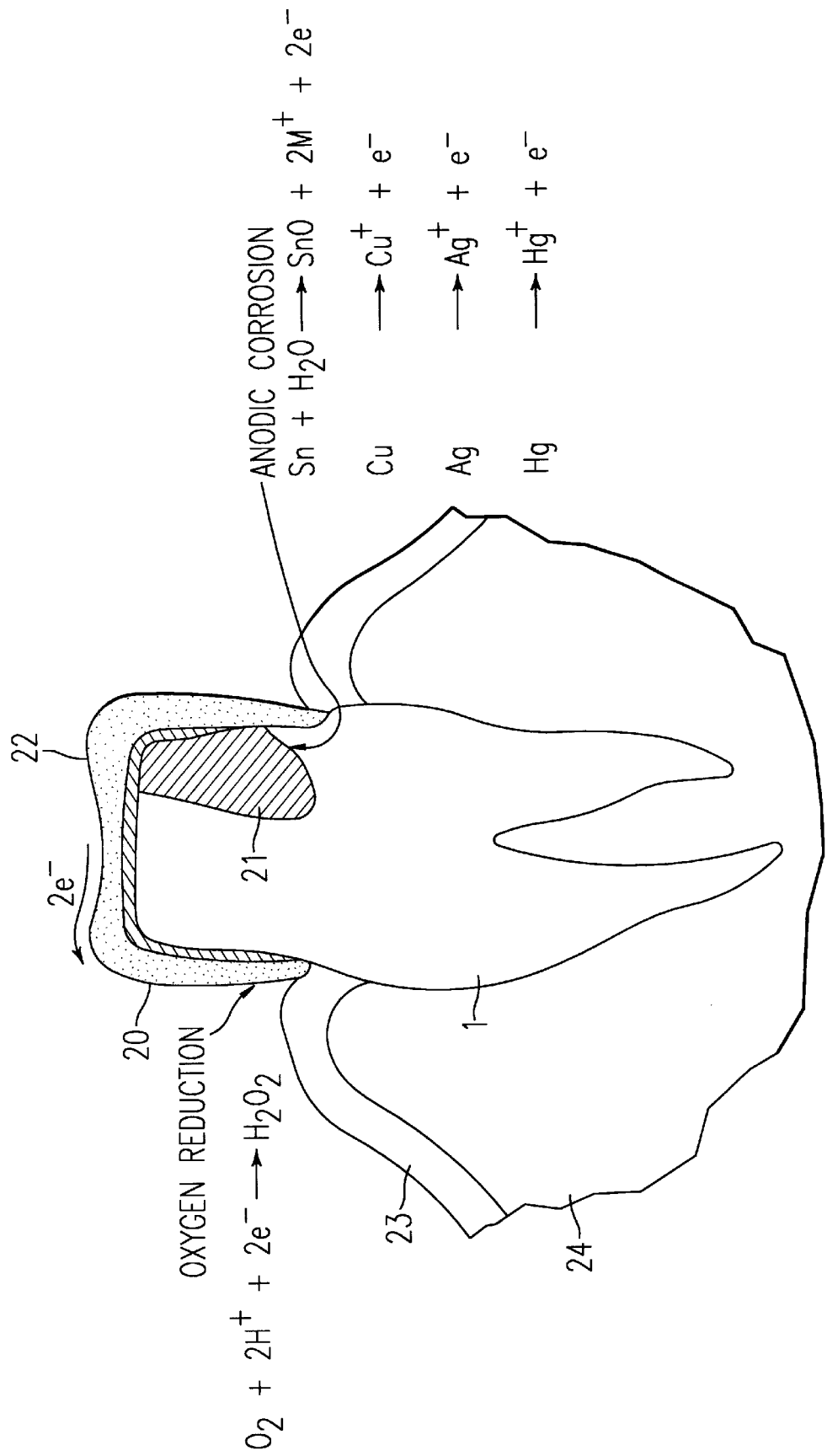
FIG. 2 shows a cross section through a tooth, with a chemical reaction taking place.

The electrochemical reactions determining the potential are explained with reference to FIG. 2. FIG. 2 shows a cross section through a tooth 1 with a gold crown 20, an amalgam filling 21 and a layer of cement 22 extending between the amalgam filling 21, or the tooth 1, and the gold crown 20. The tooth 1 is incorporated in the bone 24 and surrounded by gum 23.

The potentials measured with the device according to FIG. 1 and listed in Table 1 can be explained in simplified form as follows.

It is assumed that the electrode potential of gold crowns and gold bridges is determined essentially by an electrochemical reaction, which can be described as reduction of oxygen to hydrogen peroxide. Gold is in fact a rather poor catalyst for the decomposition of peroxide and for this reason the reduction is suppressed until the-end stage water.

$$O_2 + 2H^+ + 2e^- \rightleftarrows H_2O_2$$

With identical activities of $O_2$ and $H_2O_2$, the theoretical electrode potential (with respect to a standard hydrogen electrode) of this reaction is given by $$E = 0.682 - 0.059 \, \text{pH}$$

The saliva of the oral cavity or the body fluid in the gum serves as the electrolyte. At a pH of 6, it is then possible to calculate, for example, a potential of E=0.328 volts.

The potential of a silver/silver chloride electrode, on the other hand, is determined by the electrode process $$AgCl + e^- \rightleftarrows Ag + Cl^-$$

and the theoretical electrode potential (with respect to a standard hydrogen electrode) is $$E = 0.222 = 0.059 \, \log(Cl^-)$$

where (Cl⁻) designates the concentration (or more precisely the activity) of the chloride ions in the electrolyte. For a 0.01 molar NaCl solution, it is thus possible to calculate a potential of 0.340 volts.

It will be appreciated from the above that the potential of a gold electrode and that of an Ag/AgCl reference electrode lie very close to one another under these conditions. The theoretical voltage difference between these two electrodes is only −0.012 volts. The gold electrode is negative with respect to the Ag/AgCl reference electrode.

This theoretical calculation is in good agreement with the experimental findings. For a gold electrode dipped in air-saturated 0.01 molar sodium chloride solution, we observed, in laboratory tests using an Ag/AgCl reference electrode in the same solution, a voltage difference of −0.020 volts. For gold alloys such as are customary in dentistry, the measured values were −0.030 to −0.050 volts. Such values would also be expected theoretically in vivo, i.e. in the saliva of the oral cavity. The experimental results confirm this, with the proviso that the oxygen reduction largely determines the potential.

It has in the meantime been recognized that the potential of gold crowns and bridges can be influenced by anodic electrochemical processes which take place (hidden) under crowns or bridges. One such anodic process is, for example, the anodic oxidation (corrosion) of amalgam. Other anodic processes are the anodic oxidation of the inner surface of the gold crown or bridge or the anodic oxidation of organic material (food residues or decomposition products of the gum). All these anodic reactions produce electrons which in turn serve for oxygen reduction. In the case of amalgam corrosion, the anodic processes can be described as follows

| Sn (in amalgam) | + H₂O | → | SnO + 2H⁺ + 2e⁻ |
|---|---|---|---|
| Cu (in amalgam) | | → | Cu⁺ + e⁻ |
| Hg (in amalgam) | | → | Hg₂²⁺ + 2e⁻ |
| Ag (in amalgam) | | → | Ag⁺ + e⁻ |

The electrons produced flow through the gold crown or bridge to the site of the oxygen reduction and are there used up:

$$O_2 + 2H^+ + 2e^- \rightarrow H_2O_2$$

By means of the above coupled reactions, a so-called mixed potential is impressed on the gold crown or bridge. By means of the (internal) current flow, the potential of the gold crown (oxygen electrode) is reduced to a lower value. This mechanism explains why the potential of a gold crown or bridge is lower in the presence of anodic reactions. (See FIG. 2).

As will be seen from the experimental results in Table 1, potentials lower than −0.150 volts point to the presence of corroding amalgam if a silver/silver chloride electrode or a silver/silver chloride reference electrode 9 is used as the active part 10.

The device according to the invention and the method therefore permit a diagnosis of the state of the tooth under a tooth bridge or tooth crown. If the potential measurement using a silver/silver chloride reference electrode shows a value which is lower than −0.150 volts, the tooth crown or tooth bridge should be removed for the purpose of treating the underlying tooth.

For investigations on tooth crowns which cover more than one tooth, or for tooth bridges which connect teeth with one another metallically conductively, account must be taken of the fact that the measured potential is a mean value for the teeth concerned.

If, however, the measured value points to the presence of amalgam, the metallically conductively connected teeth or crowns should first be separated so that the teeth can be measured and assessed individually.

The measurement then shows which teeth should be restored first.

Before carrying out a measurement with the device according to the invention, it may be advantageous to apply a gelled electrolyte in the area of the tooth crown 2 or tooth bridge 2 to be measured and/or in the area of the active part 10 of the reference electrode 9.

The active part 10 of the reference electrode 9 can be surrounded by a gaze, pad or tissue which is wetted with a calibrated solution of chloride ions. The dental reference electrode 9 can have a absorbent sheet 41 which is wetted with a calibrated solution of chloride ions.

TABLE I

| Case Number | Patient | Type of prosthesis | Ceramic Covering | Potential (Volts) | State |
| --- | --- | --- | --- | --- | --- |
| 1 | A | Bridge | without | −0.200 | Corroded gold crown inside; amalgam decomposed |
| 2 | A | Bridge | without | −0.200 | Corroded gold crown inside; amalgam decomposed |
| 3/4 | A | Crown | without | −0.215 | Strongly corroded gold crown inside; amalgam residues |
| 5 | A | Bridge | with | −0.140 | Satisfactory, no amalgam |
| 6 | A | Bridge | with | −0.225 | strongly corroded; amalgam residues |
| 7 | B | Crown | without | −0.166 | Slightly corroded cold crown inside; amalgam slightly decomposed |
| 8 | B | Crown | without | −0.060 | Good, no amalgam |
| 9 | B | Crown | without | −0.160 | Mildly corroded amalgam |

What is claimed is:

1. A dental device for determining the state of an at least partially metal tooth crown or tooth bridge of a tooth to detect the presence of amalgam, comprising:

a scanning electrode with which an electrical contact to the tooth crown or tooth bridge can be established, an active part of a reference electrode, which active part is surrounded by a liquid absorbing device which absorbs a liquid, and which active part and the liquid absorbing device which absorbs the liquid can be placed in a mouth, and a voltage meter which can be connected electrically to the scanning electrode and the reference electrode and allows their potential difference to be measured.

2. The device as claimed in claim 1, wherein the scanning electrode has an electrical contact point, and wherein at least the surface of the contact point comprises of gold, a gold alloy or a material similar to that of the tooth crown or tooth bridge.

3. The device as claimed in claim 2, wherein the contact point is connected to an electrical lead, and wherein the lead is arranged to run electrically insulated through the scanning electrode.

4. The device as claimed in claim 1, wherein the active part of the reference electrode comprises metal/metal chloride.

5. The device as claimed in claim 4, wherein the reference electrode has an active part which comprises of silver and whose surface is coated with silver chloride.

6. The device as claimed in claim 1, wherein the active part is connected to an electrical lead, wherein the lead is arranged to run electrically insulated through the reference electrode, and wherein the reference electrode is designed to be fitted in a lower jaw, the active part coming to lie in the mouth.

7. The device as claimed in claim 1, wherein the voltage meter (12) has an input resistance of more than $10^6 \Omega$.

8. The device as claimed in claim 1, wherein the liquid absorbing device is a gauze, a pad or a tissue.

9. The device as claimed in claim 8, wherein said gauze, pad or tissue is wetted with a calibrated solution of chloride ions.

10. A method for determining the state of an at least partially metal tooth crown or tooth bridge of a tooth to detect the presence of amalgam, in which a liquid absorbing device which absorbs a liquid and which surrounds an active part is wetted with a calibrated solution of chloride ions, comprising the steps of:

placing the active part and the liquid absorbing device which absorbs the liquid as part of a disposable reference electrode in a mouth, establishing an electrical contact to the tooth crown or tooth bridge using a scanning electrode, and measuring a potential difference between the scanning electrode and the active part of the reference electrode using a voltage meter.

11. A method for determining the state of an at least partially metallic tooth crown or bridge as claimed in claim 10, wherein said liquid absorbing device which absorbs a liquid is a gauze, pad or tissue.

12. The method as claimed in claim 10, wherein if the active part of the reference electrode comprises of silver coated with silver chloride, it is possible, at voltages of lower than −150 millivolts, to conclude that there is an undesired electrochemical reaction present under the tooth crown or the tooth bridge.

13. The method as claimed in claim 10, wherein in the case of a metal tooth crown or tooth bridge which is coated with porcelain or ceramic, a hole is bored through the porcelain or ceramic, and wherein the contact pin of the scanning electrode is introduced into the hole and an electrical contact is thereby established between the scanning electrode and the metal tooth crown or tooth bridge.

14. The method as claimed in claim 10, wherein a gelled electrolyte is applied in the area of the tooth crown or tooth bridge (2) to be measured and/or in the area of the active part of the reference electrode.

15. The method as claimed in claim 10, wherein the pH value and the sodium chloride concentration of the saliva are stabilized prior to the measurement procedure by rinsing the oral cavity with a buffered sodium chloride solution.

16. A dental reference electrode for electrochemical potential measurement in the oral cavity, said reference electrode comprising:

an electrochemically active part comprising a silver wire coated with silver chloride, the silver wire being designed in the form of a single or multiple loop.

17. The dental reference electrode as claimed in claim 16, wherein the active part is surrounded by a liquid absorbing device.

18. The dental reference electrode as claimed in claim 16, further comprising an absorbent sheath which covers the active part.

19. The dental reference electrode as claimed in claim 18, wherein the absorbent sheath is made of electrically insulating fibers.

20. The dental reference electrode as claimed in claim 18, further comprising a plastically deformable shaft in the inside of which an electrical connection, connecting the active part to a plug socket, is arranged to run electrically insulated from the outside.

21. The dental reference electrode as claimed in claim 16, wherein the silver wire has a diameter of between 0.6 mm and 1.2 mm.

22. The dental reference electrode as claimed in claim 20, wherein the electrical connection running through the inside of the shaft comprises silver wire which is joined to the plug socket at a rear end of the shaft, and wherein the silver wire is doubled back in the shaft.

23. The dental reference electrode as claimed in claim 16, wherein the silver chloride layer on the electrochemically active part has a thickness of between 1 µm and 5 µm.

24. The dental reference electrode as claimed in claim 23, wherein the silver chloride layer on the electrochemically active part is produced by anodic oxidation in dilute chloride solution.

25. The dental reference electrode as claimed in claim 20, wherein the shaft has a silicone tubing as an external insulator.

26. The dental reference electrode as claimed in claim 21, wherein the silver wire, at a front end of the shaft, is sealed into the electrical insulation of the shaft by a silicone adhesive.

27. The dental reference electrode as claimed in claim 18, wherein the absorbent sheath comprises a felt made up of cotton fibers.

28. The dental reference electrode as claimed in claim 27, wherein this felt has a thickness of more than 0.5 mm.

29. The dental reference electrode as claimed in claim 27, wherein this felt can absorb more than 0.1 g of water per $cm^2$.

30. The dental reference electrode as claimed in claim 18, wherein the absorbent sheath is wetted with a calibrated solution of chloride ions.

* * * * *